US012683010B2

(12) United States Patent　　　(10) Patent No.:　US 12,683,010 B2
Juhoor et al.　　　　　　　　　　　　(45) Date of Patent:　　　Jul. 14, 2026

(54) METHOD OF IDENTIFICATION OF RADIOTHERAPY TARGETS FOR TREATING AND PREVENTING CARDIAC ARRHYTHMIAS

(71) Applicant: INHEART, Pessac (FR)

(72) Inventors: Mehdi Juhoor, Pessac (FR);
　　　　　　　Jean-Marc Peyrat, Pessac (FR)

(73) Assignee: INHEART, Pessac (FR)

( * ) Notice:　Subject to any disclaimer, the term of this patent is extended or adjusted under 35 U.S.C. 154(b) by 406 days.

(21) Appl. No.: 18/212,793

(22) Filed:　　Jun. 22, 2023

(65)　　　　Prior Publication Data

US 2023/0420113 A1　　Dec. 28, 2023

(30)　　Foreign Application Priority Data

Jun. 23, 2022　　(EP) ..................................... 22180628

(51) Int. Cl.
　　*G16H 30/40*　　　(2018.01)
　　*G06T 7/11*　　　　(2017.01)
　　*G06T 17/20*　　　(2006.01)
(52) U.S. Cl.
　　CPC ............... *G16H 30/40* (2018.01); *G06T 7/11* (2017.01); *G06T 17/205* (2013.01); *G06T 2207/30048* (2013.01)
(58) Field of Classification Search
　　CPC . G06T 2207/10081; G06T 2207/10088; G06T 7/0012; G06T 2210/41; G06T 2219/2021; G06T 19/20; G16H 20/40
　　See application file for complete search history.

(56)　　　　　References Cited

U.S. PATENT DOCUMENTS

2006/0045328　A1*　3/2006　Jacob ...................... G06T 19/00
　　　　　　　　　　　　　　　　　　382/128
2011/0019892　A1*　1/2011　Rahn ...................... G06T 19/00
　　　　　　　　　　　　　　　　　　382/131

(Continued)

FOREIGN PATENT DOCUMENTS

WO　　WO2021/163227　A1　　8/2021

OTHER PUBLICATIONS

Neher, P., et al: "Automatic Segmentation of Cardiac CTs—Personalized Atrial Models Augmented with Electrophysiological Structures", Lecture Notes in Computer Science, 2022, pp. 80-87, vol. 6666.

(Continued)

*Primary Examiner* — Michael L Burleson
(74) *Attorney, Agent, or Firm* — Greer, Burns & Crain, Ltd.

(57)　　　　　ABSTRACT
A method for identifying radiotherapy targets for treating cardiac arrhythmias, which comprises: receiving at least one 3D mapping of points each associated with at least one given feature of a patient's heart and receiving locations of at least one area to be protected, said locations being spatially registered within the reference frame of the 3D mapping; segmenting at least a region in said at least one 3D mapping with selecting a plurality of points of the 3D mapping whose at least one associated given feature matches a predetermined criterion; cropping said segmented region in the 3D mapping with unselecting a plurality of points of the segmented region whose distance to said area to be protected is lower than a predetermined threshold; generating a 3D volumetric model comprising a mesh computed from said cropped region and identified to said cropped region and storing said 3D volumetric model in an electronic file.

13 Claims, 8 Drawing Sheets

(56)  References Cited

U.S. PATENT DOCUMENTS

| | | | | |
|---|---|---|---|---|
| 2020/0273559 A1* | 8/2020 | Yousfi | .................... | G16H 30/20 |
| 2021/0137384 A1 | 5/2021 | Robinson et al. | | |
| 2021/0233308 A1* | 7/2021 | Barasofsky | ............. | G06T 17/20 |
| 2022/0047237 A1* | 2/2022 | Liu | ........................ | A61B 6/032 |
| 2022/0092791 A1 | 3/2022 | Dougherty et al. | | |
| 2022/0351836 A1* | 11/2022 | Johnson | ................. | G06V 10/26 |
| 2022/0362579 A1* | 11/2022 | Robinson | ............. | A61B 8/5261 |
| 2022/0369930 A1* | 11/2022 | Robinson | ............. | A61B 5/0044 |
| 2022/0370033 A1* | 11/2022 | Klingensmith | ........ | A61B 34/10 |

OTHER PUBLICATIONS

Verela, M., et al., "Novel MRI Technique Enables Non-Invasive Measurement of Atrial Wall Thickness" IEEE Trans Med Imaging, Aug. 2017, pp. 1607-1614, vol. 36, No. 8.
European Search Report dated Dec. 27, 2022 for European Application No. EP 22 18 0628.

* cited by examiner $R'_C$

METHOD OF IDENTIFICATION OF RADIOTHERAPY TARGETS FOR TREATING AND PREVENTING CARDIAC ARRHYTHMIAS

CROSS-REFERENCE TO RELATED APPLICATIONS

This application claims the benefit of priority to European patent application EP 22180628.4 filed Jun. 23, 2022, the entire disclosure if which is herein incorporated by reference.

TECHNICAL FIELD

The present invention relates to the field of localization of radiotherapy targets from medical images of a patient's heart. More particularly, the invention relates to a method for automatic identifying radiotherapy targets from a 3D mapping of a patient's heart.

BACKGROUND

Cardiomyopathies and scarring might cause cardiac arrhythmias, as ventricular tachycardia (VT). The scar from a cardiomyopathy, for instance from a previous heart attack, might form abnormal electrical circuits within the heart, which causes VT.

It is known to treat arrhythmias with an invasive catheter-based ablation. This ablation consists of inserting a catheter into the heart through veins or arteries to burn an area of the heart tissue that is causing arrhythmias. Even if this procedure is commonly used, it carries risks due to its invasive nature, its complexity and its length.

Radiation-based therapy, as stereotactic body radiotherapy (SBRT), is routinely used in oncology to non-invasively treat solid tumors. More recently, radiotherapy has been transposed to cardiology to treat cardiac arrhythmias, as ventricular tachycardia, as a variant or in complement of catheter-based ablation. Its noninvasive nature makes it possible to mitigate the disadvantages of catheter-based ablation.

Radiation-based therapy involves the delivery of one or more high doses of radiations to the area of the heart tissue causing the arrhythmias to destroy it. In this context, one of the main steps of the therapy consists of identifying the arrhythmogenic foci, and subsequently in delineating the ablation target in an image or in a 3D model of a patient's heart.

A multitude of imaging techniques, either invasive techniques as electroanatomical mapping and/or non-invasive techniques as CT-scan and MRI, can provide images and/or mapping of the patient's heart. Such images and/or mapping can be then segmented with image processing computer implemented methods to delineate ablation targets.

However, considering the extremely high amount of energy of the radiation delivered to the tissue, it is appreciated to avoid healthy tissues surrounding the target. It is moreover critical to minimize exposure of heart structures and organs, such as coronary sinus (CS) or phrenic nerve, which are to be protected.

Considering the above, there is therefore a need for a method for an automatic identification of radiotherapy targets from a 3D mapping of a patient's heart, which minimizes the risk of exposing to the radiation a structure or an organ of the patient which must be protected.

The object of the present invention is to answer to this need.

SUMMARY

For this purpose, the subject of the invention is a computer-implemented method for identifying radiotherapy targets for treating and preventing cardiac arrhythmias, the method comprising:

a. receiving at least one 3D mapping of points each associated with at least one given feature of a patient's heart and receiving locations of at least one area to be protected, said locations being spatially registered within the reference frame of the 3D mapping;

b. segmenting at least a region in said at least one 3D mapping with selecting a plurality of points of the 3D mapping whose at least one associated given feature matches a predetermined criterion;

c. cropping said segmented region in the 3D mapping with unselecting a plurality of points of the segmented region whose distance to said area to be protected is lower than a predetermined threshold;

d. generating a 3D volumetric model comprising a mesh computed from said cropped region and identified to said cropped region and storing said 3D volumetric model in an electronic file.

According to the invention, a 3D mapping of points is automatically segmented to delineate a first region of the heart tissue which approximate a radiotherapy target. The 3D mapping of points might result from one or more imaging and/or mapping techniques of the heart, from which a 3D representation of all or part of the heart is obtained. The 3D representation is associated to local features which are representative, directly, or indirectly and partly, or fully, of the presence or the absence of arrythmias. These local features might be obtained directly or computed from the 3D representation. Therefore, an appropriate segmentation method can result to the delineation of a region responsible of arrythmias. Moreover, heart structures or organs, which are to be protected from radiations, have been previously associated to areas registered within the reference frame of the 3D mapping. Consequently, in a second step, the first region approximating the target can be reduced to a second region with an appropriate cropping to minimize the risk of an exposure of these areas, and thus of said structures and organs to be protected, to the radiation. In a third step, a 3D model including a 3D representation of the second region is generated and stored in an electronic file, which might be upload to a therapy planification system or software, to prepare the radiotherapy.

In the context of the present specification, unless expressly provided otherwise, a "computer" may refer, but is not limited to, a desktop computer, a laptop computer, a tablet computer, a piece of testing equipment, a network appliance, a controller, a digital signal processor, a computational engine within an appliance, a consumer-electronic device, a portable computing device, and/or another electronic device, and/or any combination thereof appropriate to the relevant task at hand. Moreover, the method steps might be all executed on a same device. As a variant, the method steps might be executed on several devices, connected by wires or by a wireless connection.

In the context of the present specification, a "3D mapping of points" is a set of points which are spatially distributed to represent all or part of the patient's heart.

A 3D mapping of points might be a 3D model of the heart, namely one or more structured mesh, each comprising a plurality of vertices connected with each other to define a plurality of faces and/or volumes which approximate internal and/or external surfaces and/or volumes of all or part of the heart. A 3D model might be a triangle mesh or a quadrilateral mesh, or more generally a polygonal, mesh, which comprises a plurality of vertices, with edges connecting pairs of vertices and/or polygonal faces connecting a closed set of vertices. As a variant, a 3D model might be a tetrahedral mesh or a hexahedral mesh or a prism mesh, or more generally a volume mesh, which comprises a plurality of vertices, with polyhedrons connecting a closed set of polygons defined by closed set of vertices. Preferably, each vertex and/or edge and/or polygon and/or polyhedron might be labelled as being a part of a specific sub-part of the organ. A 3D model might be stored as a list of vertices each associated with spatial coordinates and with a set of connections to other vertices, or as a list of vertices associated with spatial coordinates and a list of polygons or faces each defined by a subset of vertices contained in said list of vertices, being understood that any other suitable method of storage might be used in the context of the present specification.

A 3D mapping of points might be an unstructured set of points, namely a point cloud, where each point might be or not connected to another point of the point cloud.

In the context of the present specification, said "3D mapping of points" might be (or might be computed from) one of, or a combination of two or more of: an electrophysiological map, resulting from an electrocardiogram (ECG), an anatomical and/or a functional map, resulting from as a computed tomography (CT)-scan, a positron emission tomography (PET)-scan, a single photon emission computed tomography (SPECT)-scan or a magnetic resonance imaging (MRI)-scan, and an electro-anatomical map, resulting from an invasive mapping.

In the context of the present specification, a «feature associated to a point of a 3D mapping of points of a patient's heart» might be an electrical, a physiological, a physical or a geometrical feature of an area of the heart whose location corresponds to said point. An electrical feature might be an activation time, an electric potential or a conduction velocity. A physiological feature might be a tissue density. A physical or a geometrical feature might be a tissue thickness, such as a myocardial thickness. It is understood that any other suitable local feature of the heart which is representative, directly, or indirectly and partly, or fully, of the presence or the absence of arrythmias, might be used in the context of the present specification.

In the context of the present specification, «an area to be protected» is an area including a vulnerable structure such as a part of the phrenic nerve, a part of the gastrointestinal tract, a part of a coronary artery, or a part of an implantable cardioverter defibrillator (ICD)-lead. Said area to be protected might be included into said 3D mapping of points. For instance, said area to be protected might be a mesh of a 3D model of the heart which represents said vulnerable structure. In this case, said mesh might have be previously segmented from the 3D model or might have be added to the 3D model with an appropriate registration. As a variant, said area might be a point cloud resulting from a different imaging or mapping technique than the one used to obtain said 3D mapping, said point cloud being registered within the reference frame of the 3D mapping. As another variant, said locations of the area might be spatial coordinates, within the reference frame of the 3D mapping, of a bounding box including said area.

In the context of the present specification, «a predetermined threshold» is a threshold value or a set of threshold values determined previously to the cropping step from a preset value or from a value previously set by a user. As an example, the method according to the invention might comprise a step of displaying the 3D mapping of points on a display, wherein the segmented region is displayed with a first display method, for instance with a first color, and wherein the area to be protected is displayed with a second display method, for instance with a second color. A threshold value interface selection might be then displayed, said interface being for instance a slider or an input box. Upon the selection of a threshold value by a user, the cropping step is implemented with the selected threshold value and the cropped region is then displayed, for instance with being superimposed to the segmented region with a third display method or with replacing the segmented region with the first display method. Following any change of the threshold value by the user, the cropping step might be implemented again and the new cropped region might be displayed again.

According to the invention, the predetermined threshold might be a single value to which distance between each point of the segmented region and the closest point of the area to be protected is compared. As a variant, the predetermined threshold might be a set of values each associated with one of the points of the border of the area to be protected or with one of the points of the border of the segmented region, the distance between each point of the segmented region and the closest point of the area to be protected being then compared to the threshold value associated to this point. In the case of a reception of many areas to be protected, the threshold value might be identical for each area to be protected or might be different from one area to another.

According to the invention, the 3D volumetric model might be a 3D volumetric model of the heart. It might also comprise a mesh representing said area to be protected and/or a mesh representing said segmented region.

According to a first embodiment, the 3D mapping comprises at least a mesh of a wall of the patient's heart, said mesh being generated from one or more images of the patient's heart, each vertex of said mesh is associated with at least one value of a geometrical and/or electrical feature of the wall at the heart's point corresponding to this vertex and the segmentation step comprises the selection of a plurality of vertices of said mesh from their associated values, the segmented region being determined from said selected plurality of vertices.

According to one embodiment, the method comprises a preliminary step of acquiring a 3D image and/or recording a 3D image of a patient's organ, particularly his heart or a region of his heart, the mesh being computed from said 3D image. The 3D image may be acquired directly from an image acquisition device such as a scanner or MRI. Alternatively, the 3D image may be obtained from a recording medium on which it is stored, such as a local memory or a distant database, the 3D image having been acquired beforehand the method.

For example, the step of acquiring the 3D image can be performed by tomography. These techniques are also identified as CT-scan, PET-scan, SPECT-scan or CAT-scan and are based on the measurement of X-ray absorption by the tissues of an organ. Tomography provides a plurality of 2D images each representing a slice of the organ, which are then combined to reconstruct the 3D image of the anatomical structure of the observed organ. The 3D image comprises a volumetric distribution of pixels, or voxels.

The method according to the invention can thus comprise a 3D modeling step of the 3D image of the organ to generate a 3D model forming then the 3D mapping. The 3D modelling step comprises a modeling step of at least one layer or one wall of the organ shown in the 3D image, such as an inner face and an outer face of the layer of the organ. Said 3D model might be a mesh, especially a polygonal or a polyhedron mesh, of said layer, especially of said inner and outer faces.

In an example, the method according to the invention can include a step of segmenting one or more regions of interest in the 3D image or 3D model.

According to one embodiment, the method according to the invention comprises a sub-step of segmenting a plurality of volumes in the 3D image or in the 3D model according to their thickness, in particular following a comparison of their thickness to a plurality of thickness levels, each voxel or each vertex being labelled according to the thickness of the volume to which it belongs. Preferably, an image processing method is implemented to detect, segment or extract at least two volumes from the 3D image or from the 3D model by considering for each voxel of the 3D image or for each vertex of the 3D model the thickness of the latter and by comparing this thickness to a maximum threshold or to different thickness levels. For example, the volumes can be segmented according to thickness levels of 1 mm, 2 mm, 3 mm, 4 mm and 5 mm.

The method of the invention allows to consider for example the wall of the heart, better known as the myocardium. In this case, the 3D image or the 3D model of the heart can be segmented into different volumes according to a myocardial thickness criterion, the 3D model representing therefore a thickness map of the heart.

According to an embodiment, each vertex of said mesh is associated with a thickness of the wall at the heart's point corresponding to this vertex and the segmentation step comprises the selection of a plurality of vertices of said mesh which are associated to a thickness lower than a predetermined thickness threshold.

In this way, the segmentation step results in a segmented region of the myocardium whose thickness is lower than the thickness threshold.

According to an embodiment, said mesh comprises at least one first plurality of vertices that have been previously segmented and labelled as a target and the segmentation step comprises the selection of a second plurality of vertices connected to said first plurality of vertices of said mesh from their associated values, the segmented region being determined from the first and the second pluralities of vertices.

Said first plurality of vertices might be associated to an isthmus, a target of a previous intervention or a scar, whose location might be identified automatically by a region of interest identification method. Its location might also be identified manually by a user or it might have been priorly stored in a recording medium from which it is obtained.

For instance, the method according to the invention might comprise a step of detecting at least one region of interest in the 3D image or in the 3D model, by identifying for example at least one region of lower thickness comprised between two regions of greater thickness.

Optionally, the method according to the invention comprises a step of classifying each region of interest by means of:
the thickness of this region of interest, compared to the thickness of two adjacent areas,
the width of this region of interest, formed by the spacing of said adjacent zones, its length, defined by the arrangement of adjacent zones, the topology of the entrance and/or exit of said region of interest, such as the funnel formed by the two adjacent zones.

One can note that several geometric criteria might be taken together and combined in order to refine the classification of regions of interest.

According this embodiment, the selection of a second plurality of vertices connected to said first plurality of vertices of said mesh from their associated values might be implemented from any suitable region growing method, with recursively considering first vertices as seed points and recursively considering neighbors of the first vertices with estimating whether they should be considered as second vertices upon their associated values.

According to an embodiment, said mesh comprises at least one plurality of vertices that have been previously segmented and labelled as the area to be protected, said plurality of vertices forming a location of the area to be protected. Said vertices might be vertices of the original 3D model of the heart which have been segmented, automatically or manually, as an area of the heart to be protected, as a coronary sinus, or vertices of a 3D model of another organ of the patient, as a phrenic nerve, which have been registered with the reference frame of the original 3D model of the heart.

As an example, the method according to the invention comprises a step of detection and classification of at least one tubular structure in the 3D image or in the 3D model of the heart. More precisely, the step of detection and classification of a tubular structure might comprise a manual or an automatic detection of circles and/or of ellipses in at least a subset of 2D images composing the 3D image, each pixel of a 2D image belonging to a detected circle or a detected ellipse being classified as belonging to a detected tubular structure, and the pixels of two 2D images belonging to detected tubular structures with a generally identical shape and/or with generally identical dimensions and/or being generally positioned in the same area in the 2D images being classified as belonging to a same detected tubular structure. Preferably, the step of detection and classification of a tubular structure might comprise an interpolation of the detected tubular structure to the rest of 2D images.

According to a second embodiment, the 3D mapping comprises a point cloud of a portion of the patient's heart, each point of said point cloud being computed from data received from at least one sensor of a catheter inside said portion, each point of said point cloud being associated with at least one value of a geometrical and/or electrical feature of the portion acquired by said sensor, and the segmentation step comprises the selection of a plurality of points of said point cloud from their associated values, the segmented region being determined from said selected plurality of points. As a variant, said point cloud might be computed from an ECG of the patient. Said point cloud can thus form an electrical activation map of the patient's heart.

According to one embodiment, each point of said point cloud is associated with a local activation time and/or with a local conduction velocity and wherein the segmentation step comprises the selection of a plurality of points of said point cloud which are associated to a local activation time greater than a predetermined threshold and/or with a local conduction velocity lower than a predetermined threshold.

In the context of the present specification, an electric potential might be acquired by an electrode of the catheter when it contacted or when it is located near to a portion of the heart, and an activation time of a point, whose location corresponds to this region, might be computed from the evolution of this electric potential over time. A conduction velocity might be computed from the differences in activation times of at least two or three different points.

According to one embodiment, the step of reception of locations of at least one area to be protected comprises:

a. a step of receiving a mesh of a wall of the patient's heart, said mesh being generated from one or more images of the patient's heart, and said mesh comprises at least one plurality of vertices that have been previously segmented and labelled as the area to be protected, said plurality of vertices forming a location of the area to be protected, b. a step of registering said mesh within the reference frame of the point cloud.

The registration sub-step might be implemented manually by a user or automatically by a registration method.

According to one embodiment, each vertex of said mesh is associated with at least one value of a geometrical and/or electrical feature of the wall at the heart's point corresponding to this vertex, and the segmentation step comprises the selection of a plurality of vertices of said mesh from their associated values, the segmented region being determined from a merge of the selected plurality of vertices and the selected plurality of points.

According this embodiment, each point of said point cloud might be mapped with at least one vertex of said mesh. One can thus increase the reliability of the segmentation with merging a segmentation of a 3D model of the heart, for instance based on wall thickness, and a segmentation of an electrical activation map of the heart, for instance based on activation time. For instance, a selected point of the point cloud might be part of the segmented region only whether its associated vertex of the mesh has been itself selected.

According to one embodiment, the 3D mapping comprises at least one tag located on at least one point of said point cloud, and the segmentation step comprises the selection of a first plurality of vertices of said mesh from the location of the tag and the selection of a second plurality of vertices connected to said first plurality of vertices of said mesh from their associated values, the segmented region being determined from the first and the second pluralities of vertices.

According to this embodiment, a tag, being for instance a tag of a target of a previous intervention or a tag of a detected region of interest, might be projected on the 3D model of the heart to identify said first plurality of vertices and the segmented region might be determined for instance with a region-growing method from these first vertices.

According to one embodiment, the method according to the invention might comprise a step of modification of said segmented region and/or said cropped region with a morphological operator.

In the context of the present specification, a «morphological operator» might be a geometric transformation implemented on a region which results in a modification of the shape of the region, such as an expansion of the region, a dilation of the region or an erosion of the region. One can note that the segmentation step and/or the cropping step might result in artifacts, as holes, aliasing or protrusions in the segmented region or in the cropped region or as group or cluster of points being outside of the main segmented region. Morphological operators might help to reduce these artifacts.

According to one embodiment, the method according to the invention might comprise a step of manual correction of said segmented region and/or said cropped region, for instance resulting a smoothing of the contour of said region. It so, said correction might be implemented through a drawing interface on which said region is displayed and with which a user can interact to correct said region.

According to one embodiment, said mesh of the 3D volumetric model is generated with extruding a thickness of the cropped region. For instance, whether said cropped region is a part of a mesh of a 3D model of the heart representing an inner or an outer surface of the myocardium, said cropped region might be extruded according to the thickness direction of the heart, for instance according to normal directions to said inner or outer surface, until encountering a mesh representing the outer, respectively the inner surface of the myocardium.

According to one embodiment, said 3D volumetric model might be stored in an electronic file in the digital imaging and communications in medicine (DICOM) image format.

The subject of the invention is also a computer program product recorded on a computer storage device, the computer program product including instructions that when executed by a processor cause the processor to execute the steps of the method according to invention.

The subject of the invention is also a computer-readable storage medium including portions of code of a computer program intended to be executed by the controlling unit of a therapeutic system according to the invention so as to implement the method according to invention.

The present invention will be better understood and other advantages will appear on reading the detailed description of an embodiment taken by way of non-limiting example and illustrated by the appended drawings.

DETAILED DESCRIPTION

Figure 1:
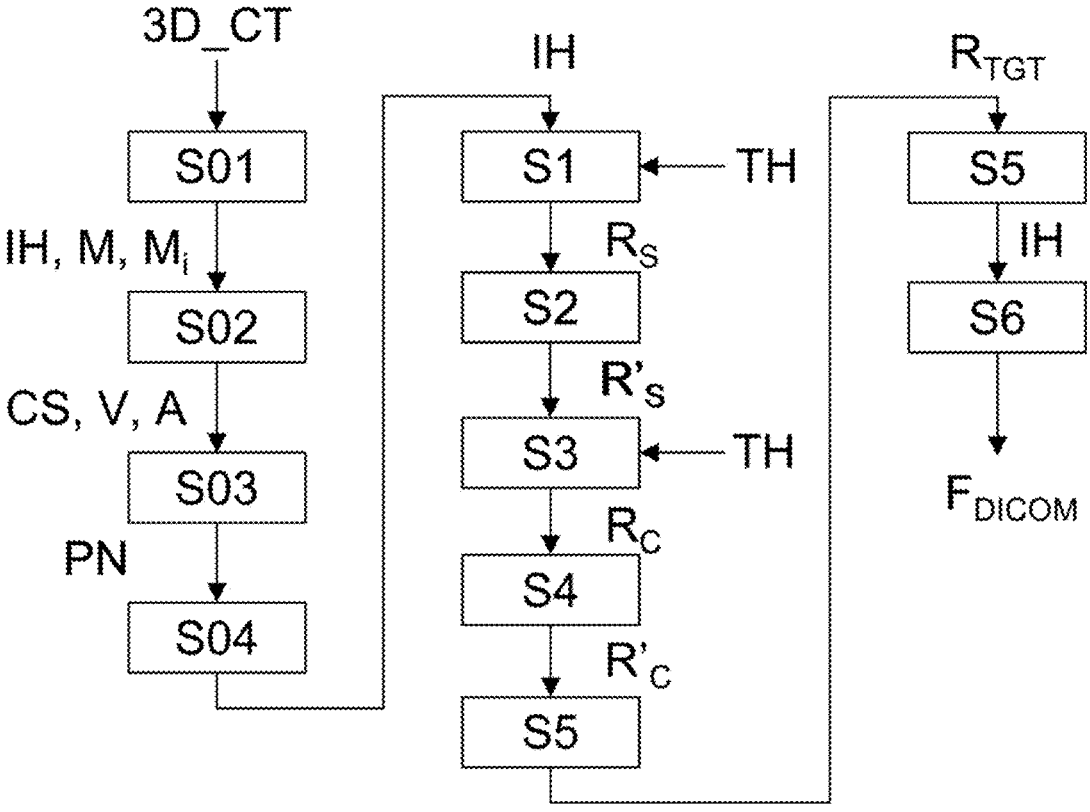
FIG. 1 is logic flow diagram that depicts a computer-implemented method, according to an embodiment of the invention.

Reference is made to FIG. 1 which shows a computer-implemented method for identifying and delineating radio-therapy targets in a patient's heart, which is at least partly executed by a computing unit of a computer equipped with a display.

In a preliminary step S01, a 3D image 3D_CT of the patient's heart has been acquired from a CT-scan method, and a 3D model IH of the patient's heart has been generated from the 3D image.

More precisely, an inner surface or layer and an outer surface or layer of the patient's heart myocardium have been modelized from the 3D image 3D_CT with defining a plurality of vertices of meshes representing said surfaces. Moreover, these vertices have been segmented, according to the thickness of the myocardium computed from these inner and outer surfaces or layers. The segmentation results at least in a mesh M of the inner surface or layer or of the outer surface or layer of the myocardium. Said mesh M comprises a plurality of superimposed sub-meshes $M_i$, with each sub-mesh corresponding to a thickness range of the myocardium.

Figure 2:
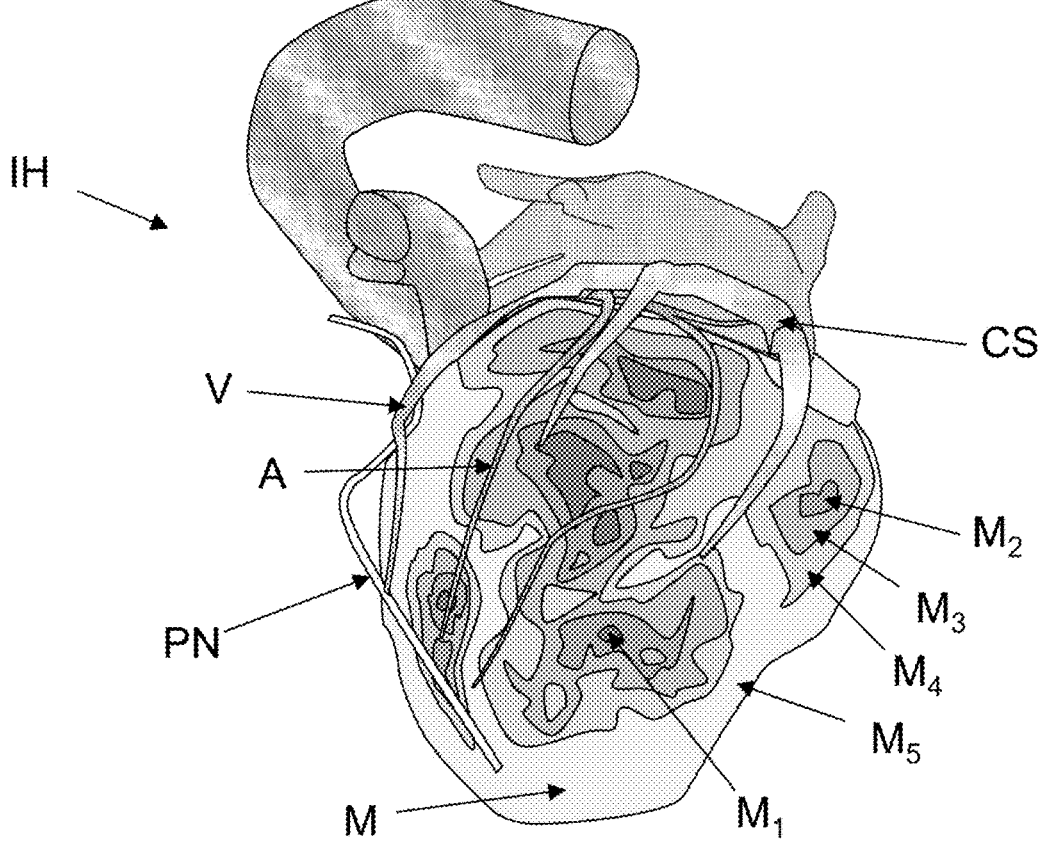
FIG. 2 shows an image of a 3D model of a heart for the implementation of the method shown in FIG. 1.

Reference is made to FIG. 2 which shows an example of a 3D model IH. The model IH comprises a mesh M comprising five superimposed thickness sub-meshes $M_1$ to $M_5$ corresponding each to a range of myocardium thickness, namely 0 to 1 mm, 1 mm to 2 mm, 2 mm to 3 mm, 3 mm to 4 mm and 4 mm to 5 mm. For description conciseness, regions of lower thickness have been depicted darker than regions of greater thickness.

In a further preliminary step S02, regions have been detected and segmented in the 3D model IH as being tubular structures and have been classified as being all or part of the coronary venous system, as the coronary sinus CS, veins V or arteries A. Said regions represent locations of areas be protected from radiations.

Moreover, in a further preliminary step S03, a mesh PN have been added to the 3D model IH. Said mesh PN represents a part of the phrenic nerve which have been segmented from another 3D image of the patient, for instance acquired from an ultrasound scan or from a MRI scan of the patient. Said mesh PN have been registered within the reference frame of the 3D model IH and added to it.

Further meshes representing vulnerable structures, as a part of the gastrointestinal tract or a part of an implantable cardioverter defibrillator (ICD)-lead, might also be added to the 3D model IH.

One can note that the step S01 to S03 might be executed by another computing unit than the one used for the rest of the method. Moreover, steps S01 to S03 might be executed fully automatically by a computing unit or with a human assistance. The resulting 3D model IH might be stored on a recording medium, such as a memory of the computer or an external memory support or a distant database through which it is accessible to the computer.

In a step S04, the 3D model IH is provided to the computing unit of the computer.

In a segmentation step S1, the computing unit selects vertices of sub-meshes Mi whose thickness is lower than a predetermined threshold TH. Said selection results in segmented regions $R_S$ in the mesh M of the model IH.

Figure 3A:
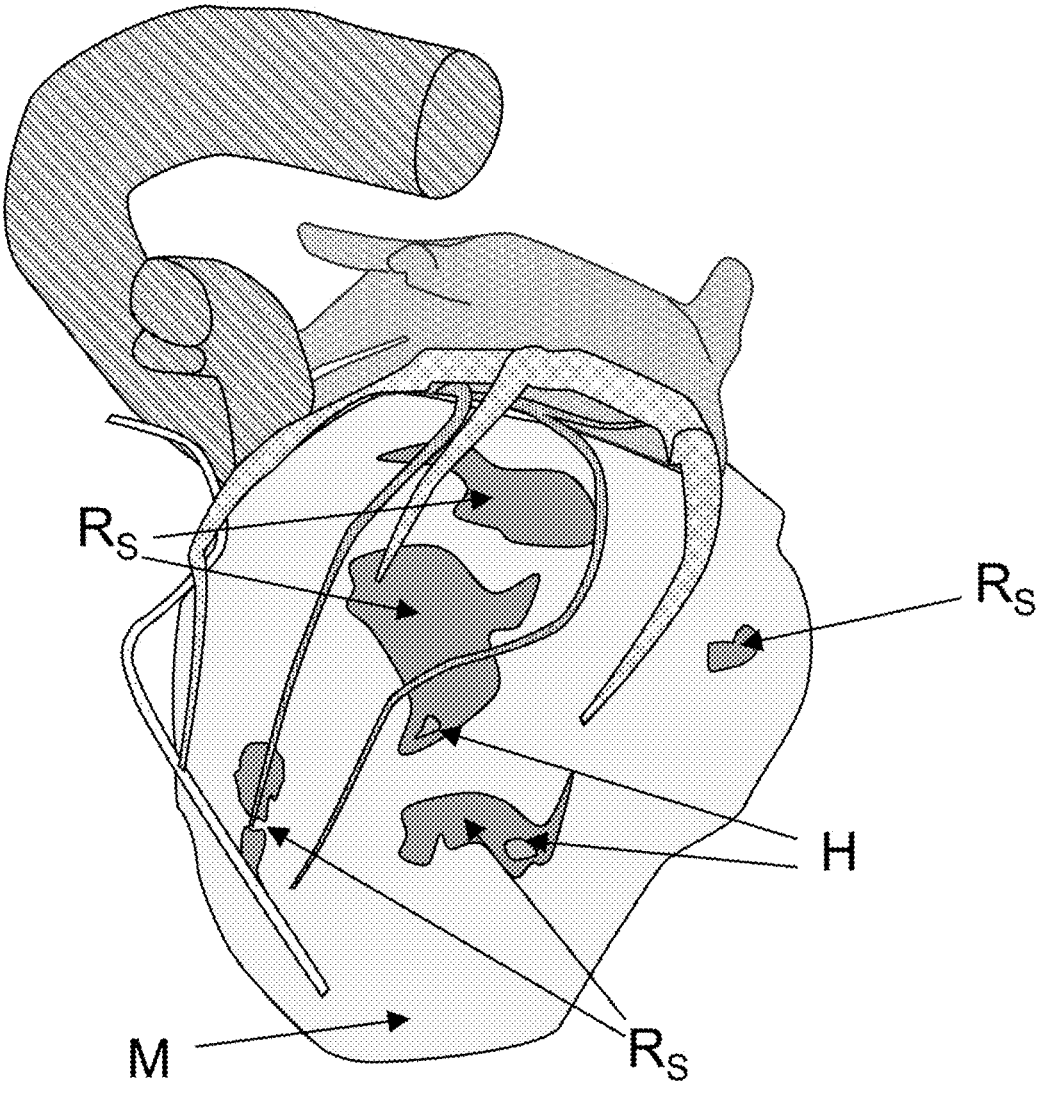
FIGS. 3A to 3E show images of the 3D model of FIG. 2 at different steps during the implementation of the method of FIG. 1.

For the purpose of the segmentation step, the computing unit might display to a user of the computer a slider or an input box to define said predetermined threshold TH. Upon the selection of a threshold value by a user, the segmentation step is implemented with the selected threshold value TH and the segmented regions $R_S$ are then displayed. As shown on FIG. 3A, in the depicted example, regions $R_S$ correspond to sub-meshes $M_1$ and $M_2$ associated to myocardium thickness lower than 2 mm. Following the selection of a new threshold value TH from the user through the slider or the input box, the segmentation step S1 is renewed with the new selected value TH.

The segmentation step S1 results in the delineation of regions of lower thickness, which are deemed to be responsible of arrythmias. These regions might be considered as an initial target for a radiotherapy.

Figure 3B:
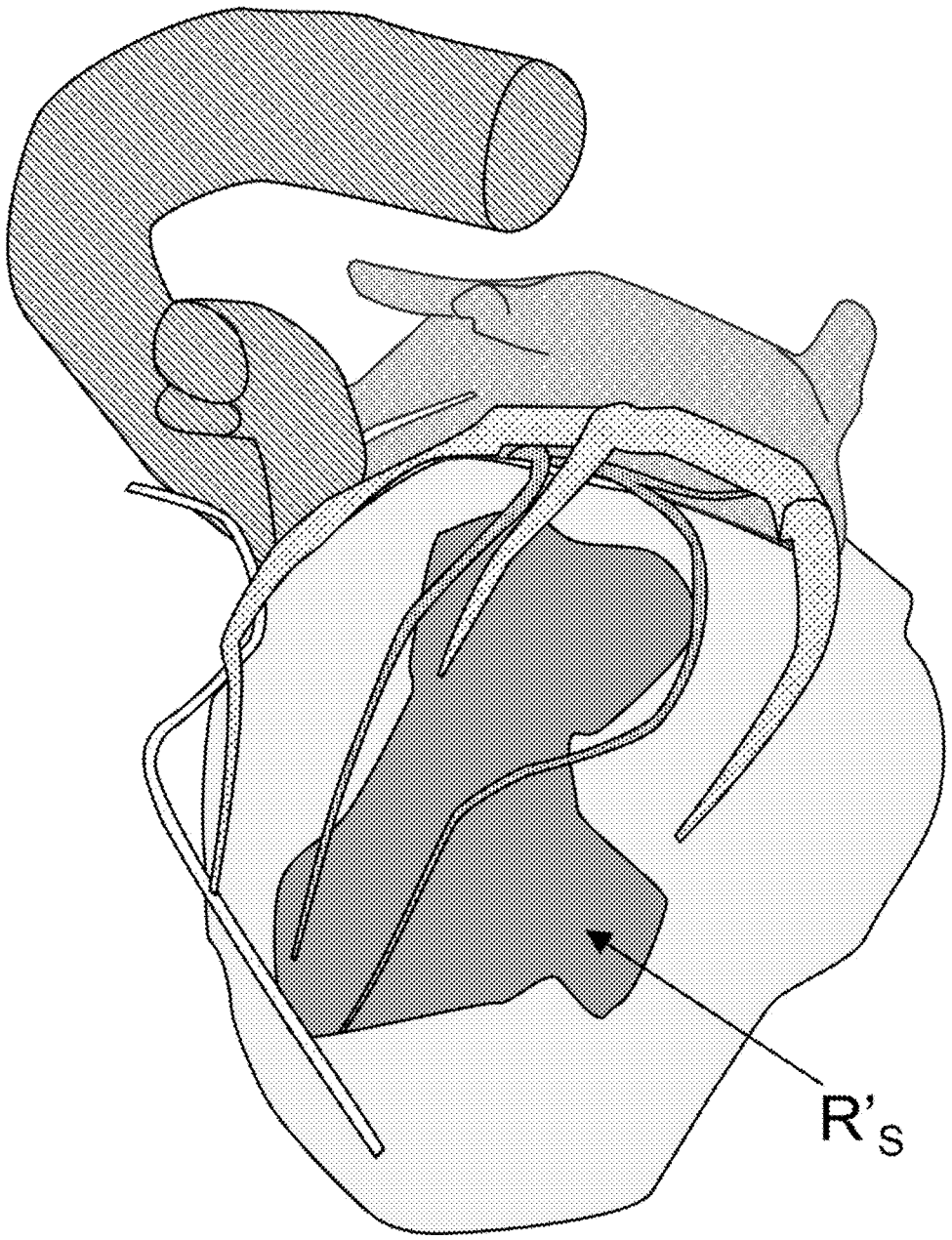

In an optional step S2, as shown on FIG. 3B, some segmented regions $R_S$ are identified as being connected together, while other regions $R_S$ are identified as being disconnected from other regions $R_S$. Morphological operators, as dilatation and/or erosion operators, and/or region growing operations are implemented to merge connected regions $R_S$ in a single segmented region $R'_S$ which excludes disconnected regions $R_S$.

In the shown example, two regions are considered to be connected upon a distance criterion, namely whether the longest distance between closest border points of these regions is lower than a preset threshold.

One can note that other methods of selection and merge of segmented regions, either manual or automatic, might be considered. For instance, one or more region of interest in the 3D model might be identified with considering segmented regions of lower thickness, and with considering their relative thicknesses regarding adjacent regions, their lengths, and their topologies. A single segmented region might be then identified with implementing a suitable region growing method applied to this region of interest.

Moreover, holes H enclosed in the regions $R_S$, which corresponds to myocardium's regions of greater thickness enclosed in myocardium's regions of lower thickness, have been removed from the single segmented region $R'_S$ with dilation operator.

One can note that, at the end of step S2, the user is free to manually correct the single segmented region $R'_S$. For the purpose of this manual correction step, the computing unit might display to the user of the computer a movable tool with which the user can interact to redraw contour of the single segmented region $R'_S$, with adding unselected vertices or with removing selected vertices.

The regions resulting from the segmentation step S1 might comprises aberration or artifacts. The step S2 helps to remove these aberration and artifacts from the initial target to improve the target delineation accuracy.

Figure 3C:
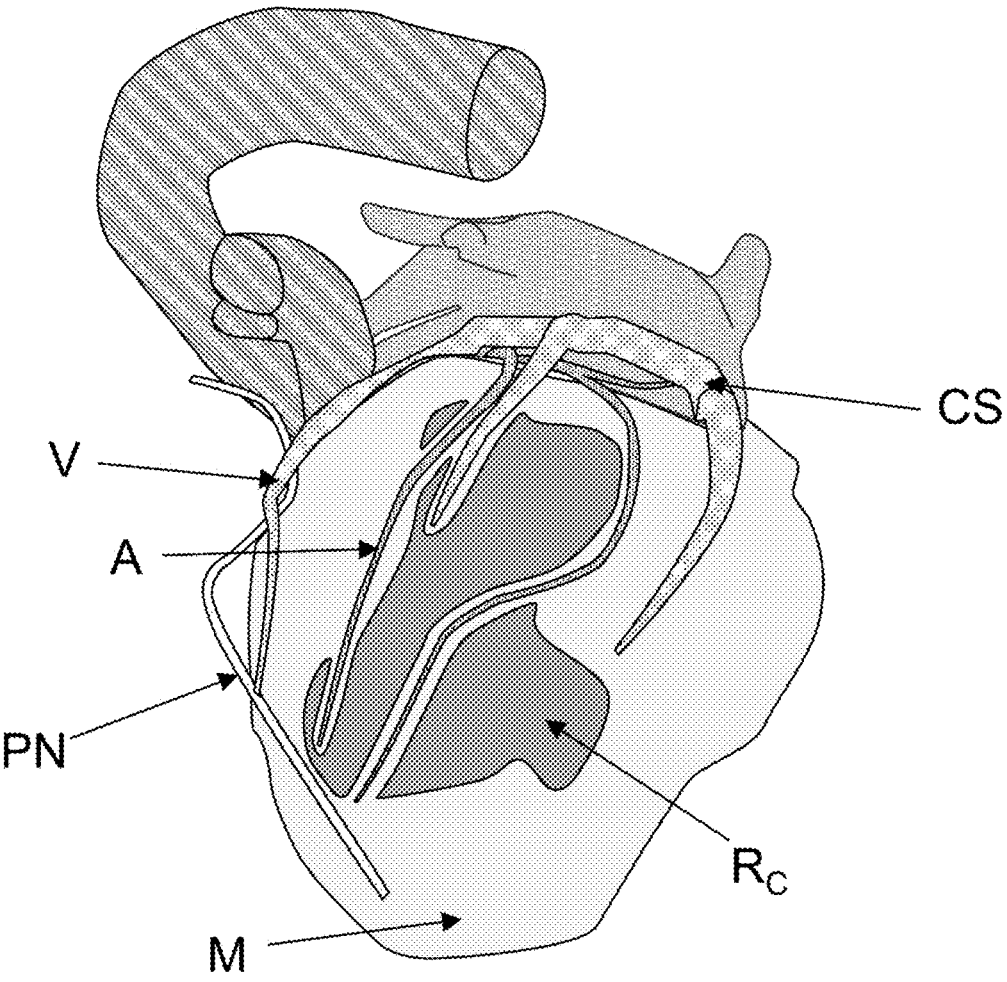

In a cropping step S3, as shown on FIG. 3C, the computing unit crops the single segmented region $R'_S$ with unselecting areas of the segmented region which are too close to the areas to be protected V, A, CS and PN.

For instance, areas to be protected V, A, CS and PN are projected on the mesh M. For each point of the projection of each area to be protected, points of the single segmented region $R'_S$ whose distance to said point are lower than a threshold value $V_{TS}$ are removed from the single segmented region $R'_S$. This operation, when performed on each area to be protected, results then in a cropped region $R_C$ separated from areas to be protected with empty spaces E.

Again, for the purpose of the cropping step, the computing unit might display to a user of the computer a slider or an input box to define said threshold value $V_{TS}$. Upon the selection of a threshold value by a user, the cropping step is executed with the selected threshold value $V_{TS}$ and the cropped region $R_C$ is then displayed. Following the selection of a new threshold value $V_{TS}$ from the user through the slider or the input box, the segmentation step S3 is renewed with the new selected value $V_{TS}$.

One can note that the threshold value might be the same value for all the areas to be protected V, A, CS and PN, resulting in constant-width empty spaces between the cropped region $R_C$ and these areas to be protected. As a variant, the threshold values might be distinct values from one area to be protected to another area to be protected. Likewise, the threshold value might be constant or evolutive along the contour of a same area to be protected.

Figure 3D:
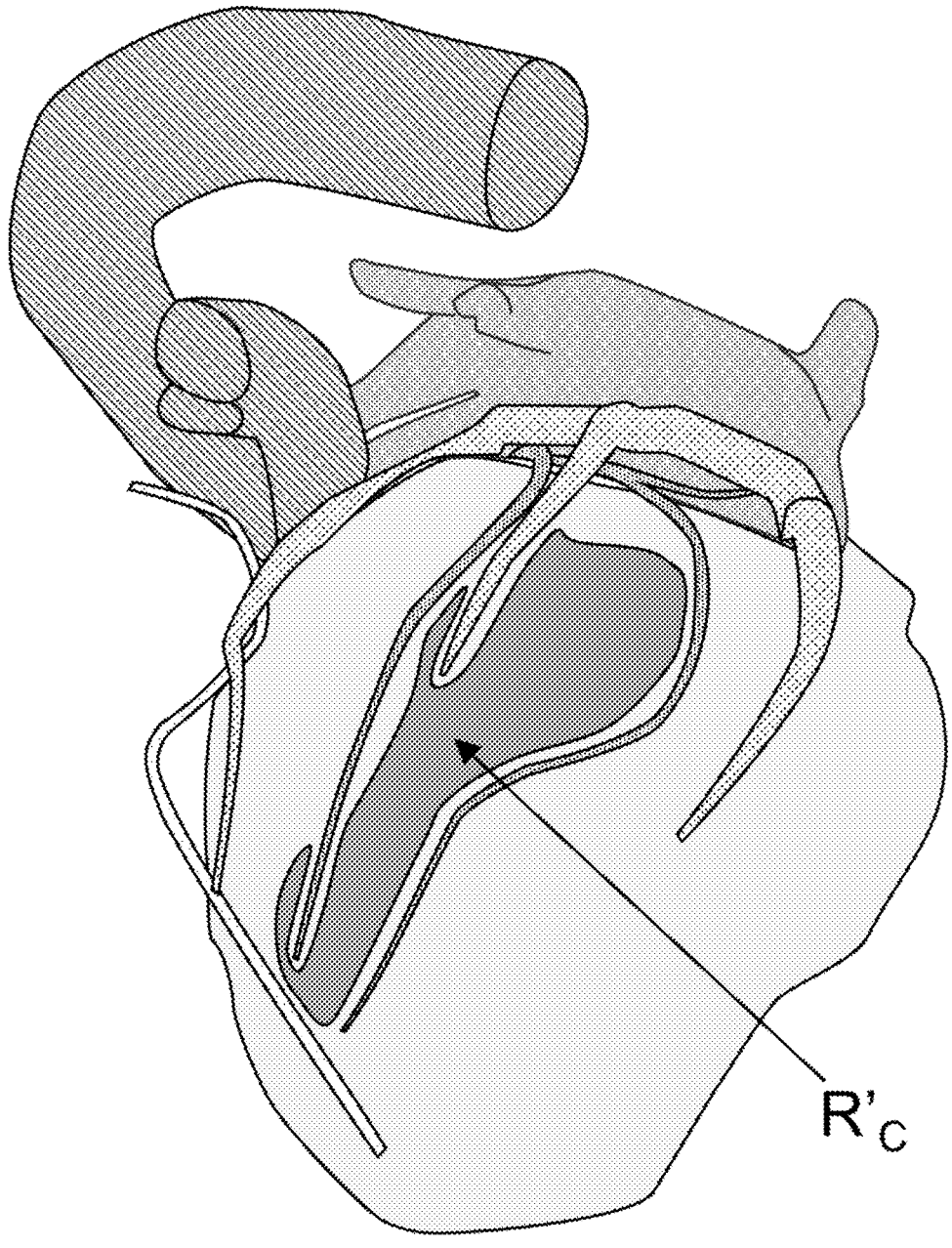
Figure 3E:
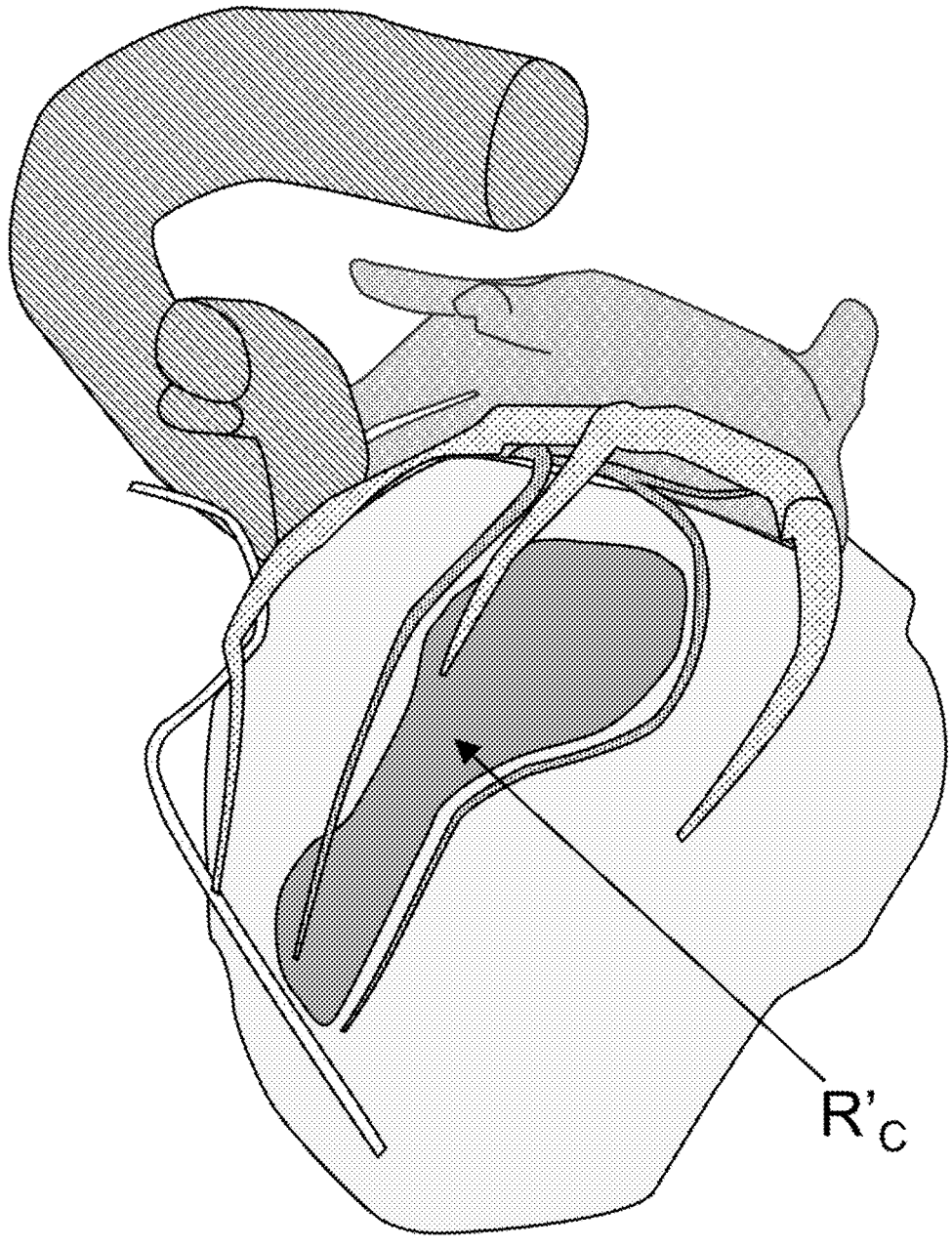
Figure 4:
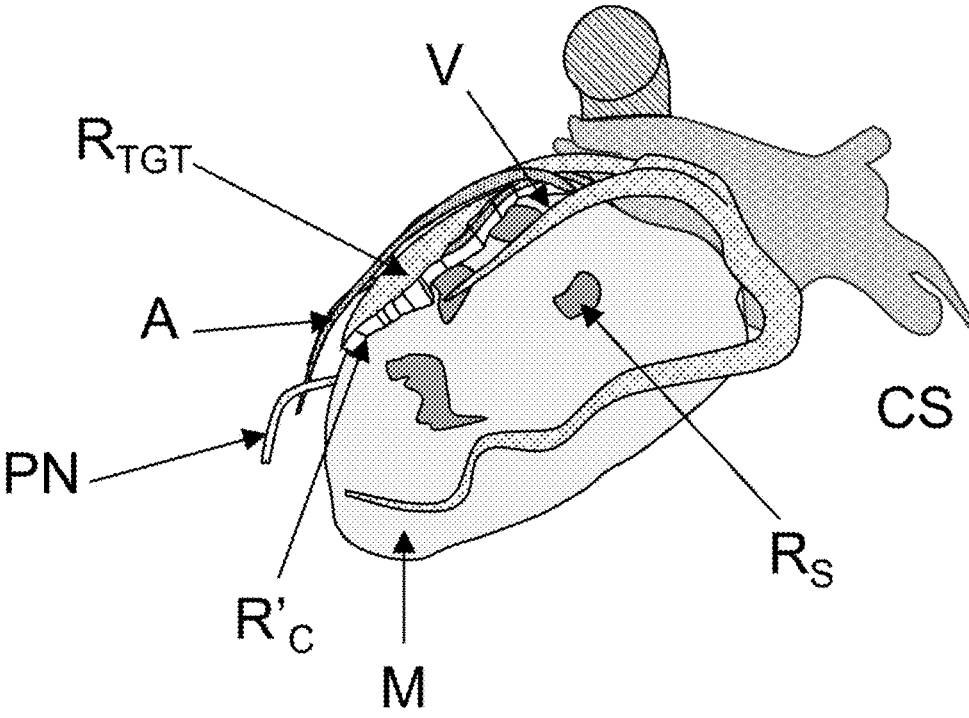
FIG. 4 shows an image of a 3D model of a heart resulting of the implementation of the method shown in FIG. 1.

In an optional step S4, as shown on FIG. 3D and FIG. 3E, morphological operators and/or region growing operations and/or manual corrections might be executed to merge connected regions of the cropped region $R_C$ or to excludes disconnected regions from the cropped region $R_C$. One can note that, following a manual correction of a user, the resulting cropped region $R'_C$ might intersect or encompass some areas to be protected.

In a modeling step S5, a mesh $R_{TGT}$ is generated from the cropped region $R'_C$ with extruding a thickness of said cropped region $R'_C$.

More precisely, in the depicted embodiment, the mesh M is a mesh of an inner layer of the myocardium. For the implementation of the step S5, each vertex of said cropped region $R'_C$ is extruded, according to a normal direction to said mesh M at this vertex, until it encounters another mesh of the 3D model IH representing an outer layer of the myocardium.

Said region $R_{TGT}$ is added to the 3D model IH.

FIGS. 3A-3E represent the 3D model IH of FIG. 2, according to another point of view, and wherein said region $R_{TGT}$ is displayed.

In a step S6, said 3D model of the heart IH is stored in an electronic file $F_{DICOM}$ with being encoded in the digital imaging and communications in medicine (DICOM) image format.

Said electronic file $F_{DICOM}$ thus comprises the model of the heart IH with added region $R_{TGT}$, initial segmented region $R_S$ and areas to be protected V, A, CS and PN.

In consequence of the above embodiment, the electronic file $F_{DICOM}$ contains a 3D delineation of a region responsible of arrythmias, which have been eroded to avoid targeting heart structures or organs, which are to be protected from radiations. The electronic file also includes the initial segmented region, to allow the user to check which parts of the initial target have been removed. The electronic file might be upload to a therapy planification system or software, to prepare the radiotherapy, or directly to a radiotherapy system.

The above description depicts an embodiment wherein locations of areas to be protected are included beforehand into the 3D model of the heart and wherein the initial target is delineated based on the thickness of a tissue of the heart. One can note that the invention also concerns embodiment wherein locations of areas to be protected are provided from another modality of acquisition, either simultaneously or sequentially and/or wherein the initial target is delineated based on another feature that is representative of the presence of an arrhythmia.

For instance, in a non-described embodiment of the invention, the 3D mapping of points in which the initial target is delineated might be an electro-anatomical map, resulting from an invasive mapping.

In this embodiment, a catheter has been introduced beforehand into the patient's heart. This catheter is a mapping catheter provided with one or more electrodes. These electrodes provide periodically to a controller local electric potential, captured on the endocardium and each associated with spatial coordinates. Said controller has generated a 3D point cloud from the signals provided by the electrodes, each point being labelled with a value of an electrical property of the endocardium computed from said electric potentials. The resulting point cloud forms therefore the electro-anatomical map. For instance, the controller might compute an activation time or conduction velocity for each point of the point cloud.

One can note that the segmentation step of the method according to this embodiment might be executed with comparing said activation or said conduction velocity to a threshold to identify regions of low voltage, slow conduction, or abnormal activity which might be responsible of arrythmias. An equivalent segmentation resulting in an initial target delineation might be executed on an electrophysiological map, resulting from an electrocardiogram.

Whether locations of areas to be protected are provided to the method according to this embodiment, these locations might be registered within the frame of reference of the 3D point cloud and the initial target might be then cropped, following the hereinabove described steps.

The methods disclosed herein may also be implemented by software programs executable by a computer system. Further, implementations may include distributed processing and parallel processing, especially for processing in parallel several or all data in the data sets.

The illustrations described herein are intended to provide a general understanding of the structure of various embodiments. These illustrations are not intended to serve as a complete description of all elements and features of apparatus, processors and systems that utilizes the structures or methods described therein. Many other embodiments or combinations thereof may be apparent to those of ordinary skills in the art upon reviewing the disclosure by combining the disclosed embodiments. Other embodiments may be utilized and derived from the disclosure, such that structural and logical substitutions and changes may be made without departing from the scope of the disclosure.

Further, the disclosure and the illustrations are to be considered as illustrative rather than restrictive, and the appended claims are intended to cover all such modifications, enhancements and other embodiments, which fall within the true spirit and scope of the description. Thus, the scope of the following claims is to be determined by the broadest permissible interpretation of the claims and their equivalents and shall not be restricted or limited by the foregoing description.

We claim:

1. A computer-implemented method for identifying radiotherapy targets for treating and preventing cardiac arrhythmias, the method comprising:

a. receiving at least one 3D mapping of points each associated with at least one given feature of a patient's heart and receiving locations of at least one area to be protected, said locations being spatially registered within the reference frame of the 3D mapping;

b. segmenting at least a region in said at least one 3D mapping with selecting a plurality of points of the 3D mapping whose at least one associated given feature matches a predetermined criterion;

c. cropping said segmented region in the 3D mapping with unselecting a plurality of points of the segmented region whose distance to said area to be protected is lower than a predetermined threshold;

d. generating a 3D volumetric model comprising a mesh computed from said cropped region and identified to said cropped region and storing said 3D volumetric model in an electronic file;

wherein the 3D mapping comprises at least a mesh of a wall of the patient's heart, said mesh being generated from one or more images of the patient's heart, wherein each vertex of said mesh is associated with at least one value of a geometrical and/or electrical feature of the wall at the heart's point corresponding to this vertex and wherein the segmentation step comprises the selection of a plurality of vertices of said mesh from their associated values, the segmented region being determined from said selected plurality of vertices; and wherein said mesh comprises at least one plurality of vertices that have been previously segmented and labelled as the area to be protected, said plurality of vertices forming a location of the area to be protected.

2. The method according to claim 1, wherein each vertex of said mesh is associated with a thickness of the wall at the heart's point corresponding to this vertex and wherein the segmentation step comprises the selection of a plurality of vertices of said mesh which are associated to a thickness lower than a predetermined thickness threshold.

3. The method according to claim 1, wherein said mesh comprises at least one first plurality of vertices that have been previously segmented and labelled as a target and wherein the segmentation step comprises the selection of a second plurality of vertices connected to said first plurality of vertices of said mesh from their associated values, the segmented region being determined from the first and the second pluralities of vertices.

4. The method according to claim 1, wherein the 3D mapping comprises a point cloud of a portion of the patient's heart, each point of said point cloud being computed from data received from at least one sensor of a catheter inside said portion, wherein each point of said point cloud is associated with at least one value of a geometrical and/or electrical feature of the portion acquired by said sensor and wherein the segmentation step comprises the selection of a plurality of points of said point cloud from their associated values, the segmented region being determined from said selected plurality of points.

5. The method according to claim 4, wherein each point of said point cloud is associated with a local activation time and/or with a local conduction velocity and wherein the segmentation step comprises the selection of a plurality of points of said point cloud which are associated to a local activation time greater than a predetermined threshold and/or with a local conduction velocity lower than a predetermined threshold.

6. The method according to claim 4, wherein the step of reception of locations of at least one area to be protected comprises:

e. a step of receiving a mesh of a wall of the patient's heart, said mesh being generated from one or more images of the patient's heart, and said mesh comprises at least one plurality of vertices that have been previously segmented and labelled as the area to be protected, said plurality of vertices forming a location of the area to be protected, f. a step of registering said mesh within the reference frame of the point cloud.

7. The method according to claim 6, wherein each vertex of said mesh is associated with at least one value of a geometrical and/or electrical feature of the wall at the heart's point corresponding to this vertex, and wherein the segmentation step comprises the selection of a plurality of vertices of said mesh from their associated values, the segmented region being determined from a merge of the selected plurality of vertices and the selected plurality of points.

8. The method according to claim 6, wherein the 3D mapping comprises at least one tag located on at least one point of said point cloud, wherein the segmentation step comprises the selection of a first plurality of vertices of said mesh from the location of the tag and the selection of a second plurality of vertices connected to said first plurality of vertices of said mesh from their associated values, the segmented region being determined from the first and the second pluralities of vertices.

9. The method according to claim 1, said method comprising a step of modification of said segmented region and/or said cropped region with a morphological operator.

10. The method according to claim 1, wherein said mesh of the 3D volumetric model is generated with extruding a thickness of the cropped region.

11. The method according to claim 1, wherein said 3D volumetric model is stored in an electronic file in the digital imaging and communications in medicine (DICOM) image format.

12. A computer-implemented method for identifying radiotherapy targets for treating and preventing cardiac arrhythmias, the method comprising:

a. receiving at least one 3D mapping of points each associated with at least one given feature of a patient's heart and receiving locations of at least one area to be protected, said locations being spatially registered within the reference frame of the 3D mapping;

b. segmenting at least a region in said at least one 3D mapping with selecting a plurality of points of the 3D mapping whose at least one associated given feature matches a predetermined criterion;

c. cropping said segmented region in the 3D mapping with unselecting a plurality of points of the segmented region whose distance to said area to be protected is lower than a predetermined threshold;

d. generating a 3D volumetric model comprising a mesh computed from said cropped region and identified to said cropped region and storing said 3D volumetric model in an electronic file;

wherein the 3D mapping comprises at least a mesh of a wall of the patient's heart, said mesh being generated from one or more images of the patient's heart, wherein each vertex of said mesh is associated with at least one value of a geometrical and/or electrical feature of the wall at the heart's point corresponding to this vertex and wherein the segmentation step comprises the selection of a plurality of vertices of said mesh from their associated values, the segmented region being determined from said selected plurality of vertices; and wherein each vertex of said mesh is associated with a thickness of the wall at the heart's point corresponding to this vertex and wherein the segmentation step comprises the selection of a plurality of vertices of said mesh which are associated to a thickness lower than a predetermined thickness threshold.

13. A computer-implemented method for identifying radiotherapy targets for treating and preventing cardiac arrhythmias, the method comprising:

a. receiving at least one 3D mapping of points each associated with at least one given feature of a patient's heart and receiving locations of at least one area to be protected, said locations being spatially registered within the reference frame of the 3D mapping;

b. segmenting at least a region in said at least one 3D mapping with selecting a plurality of points of the 3D mapping whose at least one associated given feature matches a predetermined criterion;

c. cropping said segmented region in the 3D mapping with unselecting a plurality of points of the segmented region whose distance to said area to be protected is lower than a predetermined threshold;

d. generating a 3D volumetric model comprising a mesh computed from said cropped region and identified to said cropped region and storing said 3D volumetric model in an electronic file;

wherein the 3D mapping comprises a point cloud of a portion of the patient's heart, each point of said point cloud being computed from data received from at least one sensor of a catheter inside said portion, wherein each point of said point cloud is associated with at least one value of a geometrical and/or electrical feature of the portion acquired by said sensor and wherein the segmentation step comprises the selection of a plurality of points of said point cloud from their associated 5 values, the segmented region being determined from said selected plurality of points; and wherein the step of reception of locations of at least one area to be protected comprises:

e. a step of receiving a mesh of a wall of the patient's 10 heart, said mesh being generated from one or more images of the patient's heart, and said mesh comprises at least one plurality of vertices that have been previously segmented and labelled as the area to be protected, said plurality of vertices forming a location of 15 the area to be protected, f. a step of registering said mesh within the reference frame of the point cloud.

* * * * *